US011311613B2

(12) United States Patent
Schlom et al.

(10) Patent No.: US 11,311,613 B2

(45) Date of Patent: Apr. 26, 2022

(54) DEVELOPMENT OF AGONIST EPITOPES OF THE HUMAN PAPILLOMAVIRUS

(71) Applicant: The United States of America, as represented by the Secretary, Department of Health and Human Services, Bethesda, MD (US)

(72) Inventors: Jeffrey Schlom, Potomac, MD (US); Kwong-Yok Tsang, Bethesda, MD (US)

(73) Assignee: The United States of Americans represented by the Secretary, Department of Health and Human Services, Bethesda, MD (US)

( * ) Notice: Subject to any disclaimer, the term of this patent is extended or adjusted under 35 U.S.C. 154(b) by 156 days.

(21) Appl. No.: 16/347,764

(22) PCT Filed: Nov. 6, 2017

(86) PCT No.: PCT/US2017/060109

§ 371 (c)(1),
(2) Date: May 6, 2019

(87) PCT Pub. No.: WO2018/085751

PCT Pub. Date: May 11, 2018

(65) Prior Publication Data

US 2019/0314479 A1 Oct. 17, 2019

Related U.S. Application Data

(60) Provisional application No. 62/497,064, filed on Nov. 7, 2016.

(51) Int. Cl.

*A61K 39/12* (2006.01)
*A61P 31/20* (2006.01)
*A61K 39/00* (2006.01)

(52) U.S. Cl.

CPC .............. *A61K 39/12* (2013.01); *A61P 31/20* (2018.01); *A61K 2039/5154* (2013.01)

(58) Field of Classification Search

None

See application file for complete search history.

(56) References Cited

U.S. PATENT DOCUMENTS

| | | | | |
|---|---|---|---|---|
| 8,802,076 B2 * | 8/2014 | Abraham | A61K 9/5123 | 424/85.2 |
| 2007/0014810 A1 * | 1/2007 | Baker | A61K 39/0011 | 424/186.1 |
| 2019/0134195 A1 * | 5/2019 | Jones | A61P 35/00 | |

FOREIGN PATENT DOCUMENTS

| | | | |
|---|---|---|---|
| WO | WO 03/040165 | A2 | 5/2003 |
| WO | WO 2004/098497 | A2 | 11/2004 |
| WO | WO 2005/089164 | A2 | 9/2005 |
| WO | WO 2008/147187 | A1 | 12/2008 |
| WO | WO 2009/148229 | A2 | 12/2009 |
| WO | WO 2015/106281 | A1 | 7/2015 |

OTHER PUBLICATIONS

Moschonas et al. (Accession No. GenBank ASZ83880.1, Journal of Medical Microbiology, 2017).*

Jang et al., "Identification of Novel Immunogenic Human Leukocyte Antigen-A*2402-Binding Epitopes of Human Papillomavirus Type 16 E7 for Immunotherapy Against Human Cervical Cancer," *Cancer*, 118(8): 2173-2183 (Apr. 15, 2012).

European Patent Office, International Search Report and Written Opinion in International Patent Application No. PCT/US2017/060109 (dated Dec. 22, 2017).

* cited by examiner

*Primary Examiner* — Agnieszka Boesen

(74) *Attorney, Agent, or Firm* — Leydig Voit and Mayer, Ltd.

(57) ABSTRACT

The invention provides HPV agonist epitopes, which can be used as a peptide, polypeptide (protein), and/or in a vaccine or other composition for the prevention or therapy of HPV infection and/or cancer. The invention further provides a nucleic acid encoding the peptide or polypeptide (protein), a vector comprising the nucleic acid, a cell comprising the peptide, polypeptide (protein), nucleic acid, or vector, and compositions thereof.

25 Claims, No Drawings

Specification includes a Sequence Listing.

SEQUENCE LISTING

```
<160> NUMBER OF SEQ ID NOS: 12

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Lys Leu Pro Gln Leu Cys Thr Glu Val
1               5


<210> SEQ ID NO 2
<211> LENGTH: 10
<212> TYPE: PRT
<213> ORGANISM: Artificial Sequence
<220> FEATURE:
<223> OTHER INFORMATION: Synthetic

<400> SEQUENCE: 2

Gln Leu Tyr Asn Lys Pro Leu Cys Asp Val
1               5                   10


<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Arg Thr Leu Glu Asp Leu Leu Met Gly Val
1               5                   10


<210> SEQ ID NO 4
<211> LENGTH: 9
<212> TYPE: PRT
<213> ORGANISM: Artificial Sequence
<220> FEATURE:
<223> OTHER INFORMATION: Synthetic
```

-continued

<400> SEQUENCE: 4

Lys Leu Pro Gln Leu Cys Thr Glu Leu
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Lys Ile Ser Glu Tyr Arg His Tyr Cys
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Lys Ile Ser Glu Tyr Arg His Tyr Val
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7

Gln Gln Tyr Asn Lys Pro Leu Cys Asp Leu
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Tyr Met Leu Asp Leu Gln Pro Glu Thr
1               5

<210> SEQ ID NO 9
<211> LENGTH: 9
<212> TYPE: PRT
<213> ORGANISM: Artificial Sequence
<220> FEATURE:
<223> OTHER INFORMATION: Synthetic

<400> SEQUENCE: 9

Tyr Met Leu Asp Leu Gln Pro Glu Val
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic -continued

```
<400> SEQUENCE: 10

Thr Leu His Glu Tyr Met Leu Asp Leu
1               5


<210> SEQ ID NO 11
<211> LENGTH: 9
<212> TYPE: PRT
<213> ORGANISM: Artificial Sequence
<220> FEATURE:
<223> OTHER INFORMATION: Synthetic

<400> SEQUENCE: 11

Thr Leu His Glu Tyr Met Leu Asp Val
1               5


<210> SEQ ID NO 12

<400> SEQUENCE: 12

000
```

DEVELOPMENT OF AGONIST EPITOPES OF THE HUMAN PAPILLOMAVIRUS

CROSS-REFERENCE TO RELATED APPLICATIONS

This patent application is the U.S. National phase of International Patent Application No. PCT/US2017/060109, filed Nov. 6, 2017, which claims the benefit of U.S. Provisional Patent Application No. 62/497,064, filed on Nov. 7, 2016, each of which is incorporated by reference in its entirety herein.

STATEMENT REGARDING FEDERALLY SPONSORED RESEARCH AND DEVELOPMENT

This invention was made with Government support under project number Z01BC010425 by the National Institutes of Health, National Cancer Institute. The Government has certain rights in the invention.

SEQUENCE LISTING

Incorporation-by-Reference of Material Submitted Electronically

Incorporated by reference in its entirety herein is a nucleotide/amino acid sequence listing submitted concurrently herewith and identified as follows: One 2,446 Byte ASCII (Text) file named "743376 ST25.TXT," created on May 6, 2019.

BACKGROUND OF THE INVENTION

Human papillomavirus (HPV) has been associated with the cause of several cancer types, including cervical, anal, and head and neck cancers. To date, no therapeutic HPV vaccine has been approved by the FDA.

A desire exists for a therapeutic HPV vaccine that enhances the lysis of human tumor cells.

BRIEF SUMMARY OF THE INVENTION

The invention provides a peptide comprising, consisting essentially of, or consisting of the amino acid sequence of SEQ ID NO: 1, SEQ ID NO: 2, or SEQ ID NO: 3.

In another aspect, the invention provides a polypeptide (protein) comprising the peptide; a nucleic acid encoding the peptide; a vector comprising the nucleic acid; a cell comprising the peptide, polypeptide (protein), nucleic acid, or vector; and compositions thereof.

In particular, the invention provides a HPV (e.g., HPV-16) E6 protein or polypeptide comprising the amino acid sequence of SEQ ID NO: 1 or SEQ ID NO: 2 and a HPV (e.g., HPV-16) E7 protein or polypeptide comprising the amino acid sequence of SEQ ID NO: 3.

The invention provides a method of inhibiting HPV infection in a subject comprising administering a therapeutically effective amount of a composition comprising the peptide, polypeptide (protein), nucleic acid, vector, or cell to the subject to the subject, wherein HPV infection in the subject is inhibited.

The invention also provides a method of enhancing an immune response against a HPV-associated cancer (e.g., cervical, anal, and head and neck cancers) in a subject comprising administering a therapeutically effective amount of a composition comprising the peptide, polypeptide (protein), nucleic acid, vector, or cell to the subject, wherein the immune response in the subject is enhanced.

The invention also provides a method of treating an HPV-associated cancer in a subject comprising administering a therapeutically effective amount of a composition comprising the peptide, polypeptide (protein), nucleic acid, vector, or cell to the subject.

The invention also provides a method of reducing, arresting, reversing or preventing the metastatic progression of cancer in a subject who has an HPV-associated cancer comprising administering a therapeutically effective amount of a composition comprising the peptide, polypeptide (protein), nucleic acid, vector, or cell to the subject.

The invention also provides a method of preventing or delaying the onset of an HPV-associated cancer in a subject comprising administering a therapeutically effective amount of a composition comprising the peptide, polypeptide (protein), nucleic acid, vector, or cell to the subject.

The invention further provides a method of inhibiting an HPV-associated cancer in a subject comprising (a) obtaining (isolating) lymphocytes from the subject, (b) stimulating the lymphocytes with a composition comprising the peptide, polypeptide (protein), nucleic acid, vector, or cell to the subject to generate cytotoxic T lymphocytes ex vivo, and (c) administering the cytotoxic T lymphocytes to the subject, wherein the HPV-associated cancer in the subject is inhibited.

The invention provides a method of inhibiting an HPV-associated cancer in a subject comprising (a) obtaining (isolating) dendritic cells from the subject, (b) treating the dendritic cells with a composition comprising the peptide, polypeptide (protein), nucleic acid, vector, or cell ex vivo, and (c) administering the treated dendritic cells to the subject, wherein the HPV-associated cancer in the subject is inhibited.

Additionally, the invention provides inhibiting an HPV-associated cancer in a subject comprising (a) obtaining peripheral blood mononuclear cells (PBMCs) from a subject suffering from cancer, (b) isolating dendritic cells from the PBMCs, (c) treating the dendritic cells with a composition comprising the peptide, polypeptide (protein), nucleic acid, vector, or cell ex vivo, (d) activating the PBMCs with the treated dendritic cells ex vivo, and (e) administering the activated PBMCs to the subject, wherein the HPV-associated cancer in the subject is inhibited.

The invention further provides inhibiting an HPV-associated cancer in a subject comprising (a) obtaining peripheral blood mononuclear cells (PBMCs) from a subject suffering from cancer, (b) isolating dendritic cells from the PBMCs, (c) treating the dendritic cells with a composition comprising the peptide, polypeptide (protein), nucleic acid, vector, or cell ex vivo, (d) activating the PBMCs with the treated dendritic cells ex vivo, (e) isolating T lymphocytes from the activated PBMCs ex vivo, and (f) administering the isolated T lymphocytes to the subject, wherein the HPV-associated cancer in the subject is inhibited.

The invention provides the use of adoptively transferred T cells stimulated in vitro with a composition comprising the peptide, polypeptide (protein), nucleic acid, vector, or cell to treat an HPV-associated cancer, to inhibit an HPV-associated cancer, to reduce, arrest, reverse, or prevent the metastatic progression of an HPV-associated cancer in a subject that has an HPV-associated cancer, or to prevent or delay the onset of an HPV-associated cancer.

In an additional aspect, the invention provides a method of inducing an immune response against an HPV-associated cancer in a subject comprising (a) administering to the subject a first vector (e.g., viral vector, such as poxviral vector) comprising a nucleic acid encoding the amino acid sequence of SEQ ID NO: 1, SEQ ID NO: 2, or SEQ ID NO: 3 and (b) administering to the subject a second vector (e.g., viral vector, such as poxviral vector) comprising a nucleic acid encoding the amino acid sequence of SEQ ID NO: 1, SEQ ID NO: 2, or SEQ ID NO: 3. In one embodiment, the nucleic acid encoding the amino acid sequence of SEQ ID NO: 1, SEQ ID NO: 2, or SEQ ID NO: 3 is a nucleic acid encoding an HPV (e.g., HPV-16) protein (e.g., E6 or E7) comprising the amino acid sequence of SEQ ID NO: 1, SEQ ID NO: 2, or SEQ ID NO: 3.

DETAILED DESCRIPTION OF THE INVENTION

The E6 protein promotes degradation of p53, indirectly activates telomerase, and disrupts the function of cellular phosphatase tumor suppressor PTPN13. The E7 protein inactivates pRb (retinoblastoma protein) and activates Mi2β. Together, these oncogenic alterations drive rapid cellular proliferation, suppress or downregulate key tumor suppressor proteins, and lead to cellular immortality. E6 and E7 expression is vital for malignancy and is required to maintain a malignant transformed phenotype.

Therefore, the invention provides peptides comprising an agonist epitope from the HPV (e.g., HPV-16) E6 and E7 proteins, which can be used in vaccines and other compositions for the prevention or therapeutic treatment of HPV infection and/or cancer, including, but not limited to, an HPV-associated cancer, such as cervical, anal, and head and neck cancers. In particular, the invention provides peptides, polypeptides, and proteins comprising, consisting essentially of, or consisting of the amino acid sequence of KLPQLCTEV (SEQ ID NO: 1), QLYNKPLCDV (SEQ ID NO: 2), and RTLEDLLMGV (SEQ ID NO: 3).

In another embodiment, the invention provides a polypeptide that comprises the HPV (e.g., HPV-16) E6 amino acid sequence (i.e., a HPV-16 E6 protein) or fragment thereof, wherein one or more of the corresponding amino acid residues have been replaced with one or more of the enhancer agonist epitopes SEQ ID NO: 1 or SEQ ID NO: 2. In another embodiment, the invention provides a polypeptide that comprises the HPV (e.g., HPV-16) E7 amino acid sequence (i.e., a HPV-16 E7 protein) or fragment thereof, wherein the corresponding amino acid residues have been replaced with the enhancer agonist epitope SEQ ID NO: 3.

A "polypeptide" is generally understood to be a linear organic polymer consisting of a large number of amino acid residues bonded together in a continuous, unbranched chain, forming part of, or the whole of, a protein molecule. A "peptide" is generally considered to be distinguished from a full-length protein or polypeptide on the basis of size, and, in one embodiment, as an arbitrary benchmark can be understood to contain approximately 50 or fewer amino acids, while polypeptides or full-length proteins are generally longer. However, the terms "peptide" and "polypeptide" can be used interchangeably in some embodiments to describe a protein useful in the present invention, or the term "protein" can be used generally.

The inventive peptide or polypeptide can be any suitable length. In one embodiment, a peptide of the invention has no more than 20 (e.g., no more than 19, no more than 18, no more than 17, no more than 16, no more than 15, no more than 14, no more than 13, no more than 12, no more than 11, or no more than 10) amino acid residues. The additional amino acid residues, if present, preferably are from the HPV (e.g., HPV-16) E6 or E7 protein. The additional amino acid residues can be positioned at either end or both ends of the amino acid sequence of SEQ ID NO: 1, SEQ ID NO: 2, or SEQ ID NO: 3.

A polypeptide for expression in a host cell, such as a yeast, is of a minimum size capable of being expressed recombinantly in the host cell. Accordingly, the polypeptide that is expressed by the host cell is preferably at least 25 amino acids in length, and is typically at least or greater than 25 amino acids in length, or at least or greater than 26 amino acids, at least or greater than 27 amino acids, at least or greater than 28 amino acids, at least or greater than 29 amino acids, at least or greater than 30 amino acids, at least or greater than 31 amino acids, at least or greater than 32 amino acids, at least or greater than 33 amino acids, at least or greater than 34 amino acids, at least or greater than 35 amino acids, at least or greater than 36 amino acids, at least or greater than 37 amino acids, at least or greater than 38 amino acids, at least or greater than 39 amino acids, at least or greater than 40 amino acids, at least or greater than 41 amino acids, at least or greater than 42 amino acids, at least or greater than 43 amino acids, at least or greater than 44 amino acids, at least or greater than 45 amino acids, at least or greater than 46 amino acids, at least or greater than 47 amino acids, at least or greater than 48 amino acids, at least or greater than 49 amino acids, or at least or greater than 50 amino acids in length, or at least 25-50 amino acids in length, at least 30-50 amino acids in length, or at least 35-50 amino acids in length, or at least 40-50 amino acids in length, or at least 45-50 amino acids in length, although smaller proteins may be expressed, and considerably larger proteins (e.g., hundreds of amino acids in length or even a few thousand amino acids in length) may be expressed.

In another embodiment, the invention provides a polypeptide which can be used in vaccines and other compositions for the prevention or therapeutic treatment of cancer, including but not limited to cancers that are associated with HPV (e.g., cervical, anal, and head and neck cancers), wherein the polypeptide comprises, consists essentially of, or consists of an HPV (e.g., HPV-16) E6 or E7 amino acid sequence or fragment thereof (e.g., an immunogenic domain thereof), wherein one or more of the corresponding amino acid residues of the polypeptide have been replaced (e.g., substituted) such that the polypeptide comprises one or more of the enhancer agonist epitopes of SEQ ID NO: 1, SEQ ID NO: 2, or SEQ ID NO: 3 (i.e., the polypeptide has an amino acid sequence that differs from a native, or wild-type, HPV E6 or E7 amino acid sequence in that the amino acid sequence of the polypeptide comprises one or more of the enhancer agonist epitopes, which typically involves the substitution of one, two, three or more amino acids in a given wild-type epitope sequence with a different amino acid). In one aspect of this embodiment, the polypeptide can further comprise additional HPV enhancer agonist epitopes.

Peptides and polypeptides (proteins) of the invention are, in some embodiments of the invention, used as antigens. According to the present invention, the general use herein of the term "antigen" refers to any portion of a protein (e.g., peptide, partial protein, full-length protein), wherein the protein is naturally occurring or synthetically derived or designed, to a cellular composition (whole cell, cell lysate or disrupted cells), to an organism (whole organism, lysate or disrupted cells), or to a carbohydrate, or other molecule, or a portion thereof. An antigen may elicit an antigen-specific immune response (e.g., a humoral and/or a cell-mediated immune response) against the same or similar antigens that are encountered in vitro, in vivo, or ex vivo by an element of the immune system (e.g., T cells, antibodies).

An antigen can be as small as a single epitope (e.g., SEQ ID NO: 1, SEQ ID NO: 2, or SEQ ID NO: 3 described herein), a single immunogenic domain or larger, and can include multiple epitopes or immunogenic domains. As such, the size of a protein antigen can be as small as about 8-11 amino acids (e.g., a peptide) and as large as a domain of a protein, a full-length protein, a multimer, a fusion protein, or a chimeric protein. Antigens useful in various immunotherapeutic compositions described herein include peptides, polypeptides, protein domain(s) (e.g., immunogenic domains), protein subunits, full-length proteins, multimers, fusion proteins, and chimeric proteins.

When referring to stimulation of an immune response, the term "immunogen" is a subset of the term "antigen" and, therefore, in some instances, can be used interchangeably with the term "antigen." An immunogen, as used herein, describes an antigen which elicits a humoral and/or cell-mediated immune response (i.e., is immunogenic), such that administration of the immunogen to an individual mounts an antigen-specific immune response against the same or similar antigens that are encountered by the immune system of the individual. In one embodiment, the immunogen elicits a cell-mediated immune response, including a $CD4^+$ T cell response (e.g., TH1, TH2, and/or TH17) and/or a $CD8^+$ T cell response (e.g., a CTL response).

An "immunogenic domain" or "immunological domain" of a given protein (polypeptide) can be any portion, fragment or epitope of an antigen (e.g., a peptide fragment or subunit or an antibody epitope or other conformational epitope) that contains at least one epitope that can act as an immunogen when administered to an animal. Therefore, an immunogenic domain is larger than a single amino acid and is at least of a size sufficient to contain at least one epitope that can act as an immunogen. For example, a single protein can contain multiple different immunogenic domains. Immunogenic domains need not be linear sequences within a protein, such as in the case of a Immoral immune response, where conformational domains are contemplated.

An epitope is defined herein as a single immunogenic site within a given antigen that is sufficient to elicit an immune response when provided to the immune system in the context of appropriate costimulatory signals and/or activated cells of the immune system. In other words, an epitope is the part of an antigen that is recognized by components of the immune system, and may also be referred to as an antigenic determinant. Those of skill in the art will recognize that T cell epitopes are different in size and composition from B cell or antibody epitopes, and that epitopes presented through the Class I MHC pathway differ in size and structural attributes from epitopes presented through the Class II MHC pathway. For example, T cell epitopes presented by Class I MHC molecules are typically between 8 and 11 amino acids in length, whereas epitopes presented by Class II MHC molecules are less restricted in length and may be up to 25 amino acids or longer. In addition, T cell epitopes have predicted structural characteristics depending on the specific MHC molecules bound by the epitope. Epitopes can be linear sequence epitopes or conformational epitopes (conserved binding regions). Most antibodies recognize conformational epitopes.

A "target antigen" is an antigen that is specifically targeted by an immunotherapeutic composition of the invention (i.e., an antigen, usually the native antigen, against which elicitation of an immune response is desired, even if the antigen used in the immunotherapeutic is an agonist of the native antigen). A "cancer antigen," which also is referred to as a tumor-associated antigen (TAA), is an antigen that comprises at least one antigen that is associated with a cancer, such as an antigen expressed by a tumor cell, so that targeting the antigen also targets the tumor cell and/or cancer. A cancer antigen can include one or more antigens from one or more proteins, including one or more tumor-associated proteins. Preferred enhancer agonist epitopes of the invention have an amino acid sequence of SEQ ID NO: 1, SEQ ID NO: 2, or SEQ ID NO: 3.

Examples of HPV agonist antigens discovered in the present invention are provided herein (see Examples). A peptide, protein, or polypeptide useful in the present invention comprises, consists essentially of, or consists of at least one of the enhancer agonist peptides represented by SEQ ID NO: 1, SEQ ID NO: 2, and SEQ ID NO: 3. However, other HPV agonist epitopes can be additionally included in a HPV antigen for use in the present invention. In one embodiment, a HPV agonist antigen suitable for use in the present invention comprises a HPV (e.g., HPV-16 E6 or E7) protein or polypeptide or peptide thereof having an amino acid sequence that differs from the wild-type (native) HPV protein or polypeptide or peptide thereof by at least 1, 2, 3, 4, 5, 6, 7, 8, 9, 10, 11, 12, 13, 14, 15, or more amino acid substitutions, where the amino acid substitutions introduce one or more HPV agonist epitopes into the antigen.

In addition, an HPV (e.g., HPV-16 E6 or E7) antigen useful in the present invention may include one or more additional amino acid mutations (substitutions, insertions or deletions), for example, to inactivate or delete a natural biological function of the native protein (e.g., to improve expression or enhance safety of the antigen).

The peptide or polypeptide (protein) of the invention can be prepared by any method, such as by synthesizing the peptide or by expressing a nucleic acid encoding an appropriate amino acid sequence for the peptide or polypeptide in a cell and, in some embodiments, harvesting the peptide or polypeptide from the cell. In some embodiments, the peptide or polypeptide is not harvested from the cell, such as in embodiments of the invention directed to a yeast-based immunotherapy composition, which is described in detail below. A combination of such methods of production of peptides and polypeptides also can be used. Methods of de novo synthesizing peptides and methods of recombinantly producing peptides or polypeptides are known in the art (see, e.g., Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; Sambrook et al., *Molecular Cloning: A Laboratory Manual*, 3rd ed., Cold Spring Harbor Press, Cold Spring Harbor, N.Y. 2001; and Ausubel et al., *Current Protocols in Molecular Biology*, Greene Publishing Associates and John Wiley & Sons, N Y, 1994).

The invention also provides a nucleic acid molecule comprising a nucleic acid sequence encoding the peptide or the polypeptide. The nucleic acid molecule can comprise DNA (genomic or cDNA) or RNA, and can be single or double stranded. Furthermore, the nucleic acid molecule can comprise nucleotide analogues or derivatives (e.g., inosine or phophorothioate nucleotides and the like). The nucleic acid sequence can encode the peptide or polypeptide alone or as part of a fusion protein. The nucleic acid sequence encoding the peptide or polypeptide can be provided as part of a construct comprising the nucleic acid molecule and elements that enable delivery of the nucleic acid molecule to a cell, and/or expression of the nucleic acid molecule in a cell. Such elements include, for example, expression vectors, promoters, and transcription and/or translation control sequences. Such constructs can also be referred to as "recombinant nucleic acid molecules". Suitable vectors, promoters, transcription/translation sequences, and other elements, as well as methods of preparing such nucleic acid molecules and constructs, are known in the art (e.g., Sambrook et al., supra; and Ausubel et al., supra). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a peptide or polypeptide. Similarly, the phrase "recombinant nucleic acid molecule" primarily refers to a nucleic acid molecule operatively linked to an element such as a transcription control sequence, but can be used interchangeably with the phrase "nucleic acid molecule."

The invention further provides a vector comprising the nucleic acid molecule. Examples of suitable vectors include plasmids (e.g., DNA plasmids), yeast, *listeria*, and viral vectors, such as poxvirus, retrovirus, adenovirus, adeno-associated virus, herpes virus, polio virus, alphavirus, baculorvirus, and Sindbis virus.

In a first embodiment, the vector is a plasmid (e.g., DNA plasmid). The plasmid can be complexed with chitosan.

In a second embodiment, the vector is a poxvirus (e.g., chordopox virus vectors and entomopox virus vectors). Suitable poxviruses include orthopox, avipox, parapox, yatapox, and molluscipox, raccoon pox, rabbit pox, capripox (e.g., sheep pox), leporipox, and suipox (e.g., swinepox). Examples of avipox viruses include fowlpox, pigeonpox, canarypox, such as ALVAC, mynahpox, uncopox, quailpox, peacockpox, penguinpox, sparrowpox, starlingpox, and turkeypox. Examples of orthopox viruses include smallpox (also known as variola), cowpox, monkeypox, vaccinia, ectromelia, camelpox, raccoonpox, and derivatives thereof.

The term "vaccinia virus" refers to both the wild-type vaccinia virus and any of the various attenuated strains or isolates subsequently isolated including, for example, modified vaccinia Ankara (MVA), NYVAC, TROYVAC, Dry-Vax (also known as vaccinia virus-Wyeth), PDXVAC-TC (Schering-Plough Corporation), vaccinia virus-Western Reserve, vaccinia virus-EM63, vaccinia virus-Lister, vaccinia virus-New York City Board of Health, vaccinia virus-Temple of Heaven, vaccinia virus-Copenhagen, ACAM1000, ACAM2000, and modified vaccinia virus Ankara-Bavarian Nordic ("MVA-BN").

In certain embodiments, the MVA is selected from the group consisting of MVA-572, deposited at the European Collection of Animal Cell Cultures ("ECACC"), Health Protection Agency, Microbiology Services, Porton Down, Salisbury SP4 0JG, United Kingdom ("UK"), under the deposit number ECACC 94012707 on Jan. 27, 1994; MVA-575, deposited at the ECACC under deposit number ECACC 00120707 on Dec. 7, 2000; MVA-Bavarian Nordic ("MVA-BN"), deposited at the ECACC under deposit number V00080038 on Aug. 30, 2000; and derivatives of MVA-BN. Additional exemplary poxvirus vectors are described in U.S. Pat. No. 7,211,432.

The vaccinia virus MVA was generated by 516 serial passages on chicken embryo fibroblasts of the Ankara strain of Vaccinia virus, referred to as chorioallantois virus Ankara (CVA) (see Mayr et al., *Infection,* 3: 6-14 (1975)). The genome of the resulting attenuated MVA lacks approximately 31 kilobase pairs of genomic DNA compared to the parental CVA strain and is highly host-cell restricted to avian cells (see Meyer et al., *J. Gen. Virol.,* 72: 1031-1038 (1991)). It was shown in a variety of animal models that the resulting MVA was significantly avirulent (Mayr et al., *Dev. Biol. Stand.,* 41: 225-34 (1978)). This MVA strain has been tested in clinical trials as a vaccine to immunize against smallpox in humans (see Mary et al., *Zbl. Bakt. Hyg. I, Abt. Org. B,* 167: 375-390 (1987); and Stickl et al., *Dtsch. Med. Wschr.,* 99: 2386-2392 (1974)). Those studies involved over 120,000 humans, including high-risk patients, and proved that compared to vaccinia virus-based vaccines, MVA had diminished virulence or infectiousness while still able to induce a good specific immune response. Although MVA-BN is preferred for its better safety profile because it is less replication competent than other MVA strains, all MVAs are suitable for this invention, including MVA-BN and its derivatives.

Both MVA and MVA-BN are able to efficiently replicate their DNA in mammalian cells even though they are avirulent. This trait is the result of losing two important host range genes among at least 25 additional mutations and deletions that occurred during its passages through chicken embryo fibroblasts (see Meyer et al., *Gen. Virol.,* 72: 1031-1038 (1991); and Antoine et al., *Virol.,* 244: 365-396 (1998)). In contrast to the attenuated Copenhagen strain (NYVAC) and host range restricted avipox (ALVAC), both-early and late transcription in MVA are unimpaired, which allows for continuous gene expression throughout the viral life cycle (see Sutter et al., *Proc. Nat'l Acad. Sci. USA,* 89: 10847-10851 (1992)). In addition, MVA can be used in conditions of pre-existing poxvirus immunity (Ramirez et al., *J. Virol.,* 74: 7651-7655 (2000)).

Both MVA and MVA-BN lack approximately 15% (31 kb from six regions) of the genome compared with the ancestral chorioallantois vaccinia virus Ankara ("CVA"). The deletions affect a number of virulence and host range genes, as well as the gene for Type A inclusion bodies. MVA-BN can attach to and enter human cells where virally-encoded genes are expressed very efficiently. However, assembly and release of progeny virus does not occur. MVA-BN is strongly adapted to primary chicken embryo fibroblast (CEF) cells and does not replicate in human cells. In human cells, viral genes are expressed, and no infectious virus is produced. Despite its high attenuation and reduced virulence, in preclinical studies, MVA-BN has been shown to elicit both humoral and cellular immune responses to vaccinia and to heterologous gene products encoded by genes cloned into the MVA genome (see Harrer et al., *Antivir. Ther.,* 10(2): 285-300 (2005); Cosma et al., *Vaccine,* 220): 21-29 (2003); Di Nicola et al., *Hum. Gene Ther.,* 14(14): 1347-1360 (2003); and Di Nicola et al., *Clin. Cancer Res.,* 10(16): 5381-5390 (2004)).

The reproductive replication of a virus is typically expressed by the amplification ratio. The term "amplification ratio" refers to the ratio of virus produced from an infected cell ("output") to the amount originally used to infect the cells in the first place ("input"). An amplification ratio of "1" defines an amplification status in which the amount of virus produced from infected cells is the same as the amount initially used to infect the cells, which means that the infected cells are permissive for virus infection and reproduction. An amplification ratio of less than 1 means that infected cells produce less virus than the amount used to infect the cells in the first place, and indicates that the virus lacks the capability of reproductive replication, which is a measure of virus attenuation.

Thus, the term "not capable of reproductive replication" means that an MVA or MVA derivative has an amplification ratio of less than 1 in one or more human cell lines, such as, for example, the human embryonic kidney 293 cell line (HEK293, which is deposited under deposit number ECACC No. 85120602), the human bone osteosarcoma cell line 143B (deposited under deposit number ECACC No. 91112502), the human cervix adenocarcinoma cell line HeLa (deposited at the American Type Culture Collection (ATTC) under deposit number ATCC No. CCL-2), and the human keratinocyte cell line HaCat (see Boukamp et al., *J. Cell Biol.,* 106(3): 761-71 (1988)).

MVA-BN does not reproductively replicate in the human cell lines HEK293, 143B, HeLa, and HaCat (see U.S. Pat. Nos. 6,761,893 and 6,193,752, and International Patent Application Publication No. WO 2002/042480). For example, in one exemplary experiment, MVA-BN exhibited an amplification ratio of 0.05 to 0.2 in HEK293 cells, an amplification ratio of 0.0 to 0.6 in 143B cells, an amplification ratio of 0.04 to 0.8 in HeLa cells, and an amplification ratio of 0.02 to 0.8 in HaCat cells. Thus, MVA-BN does not reproductively replicate in any of the human cell lines HEK293, 143B, HeLa, and HaCat. In contrast, the amplification ratio of MVA-BN is greater than 1 in primary cultures of chicken embryo fibroblast cells (CEF) and in baby hamster kidney cells (BHK, which is deposited under deposit number ATCC No. CRL-1632). Therefore MVA-BN can easily be propagated and amplified in CEF primary cultures with an amplification ratio above 500, and in BHK cells with an amplification ratio above 50.

As noted above, all MVAs are suitable for this invention, including MVA-BN and its derivatives. The term "derivatives" refers to viruses showing essentially the same replication characteristics as the strain deposited with ECACC on Aug. 30, 2000, under deposit number ECACC No. V00080038 but showing differences in one or more parts of its genome. Viruses having the same "replication characteristics" as the deposited virus are viruses that replicate with similar amplification ratios as the deposited strain in CEF cells, in BHK cells, and in the human cell lines HEK293, 143B, HeLa, and HaCat.

When the vector is for administration to a subject (e.g., human), the vector (e.g., poxvirus) preferably has a low replicative efficiency in a target cell (e.g., no more than about 1 progeny per cell or, more preferably, no more than 0.1 progeny per cell are produced). Replication efficiency can readily be determined empirically by determining the virus titer after infection of the target cell.

In addition to the nucleic acid molecule encoding the polypeptide (protein) or polypeptide (i.e., the peptide or polypeptide comprising, consisting essentially of, or consisting of at least one HPV enhancer agonist epitope described herein), a vector useful in the invention (e.g., a plasmid or a viral vector) also can comprise a nucleic acid sequence encoding one or more immunostimulatory/regulatory molecules, granulocyte macrophage colony stimulating factor (GM-CSF), cytokines, and/or molecules that can enhance an immune response (e.g., additional tumor-associated antigens). Exemplary additional tumor-associated antigens (TAAs, also referred to as cancer antigens) include, but are not limited to, 5-α-reductase, α-fetoprotein (AFP), AM-1, APC, April, B melanoma antigen gene (BAGE), β-catenin, Bcl12, bcr-abl, Brachyury, CA-125, caspase-8 (CASP-8 also known as FLICE), Cathepsins, CD19, CD20, CD21/complement receptor 2 (CR2), CD22/BL-CAM, CD23/$F_c$εRII, CD33, CD35/complement receptor 1 (CR1), CD44/PGP-1, CD45/leucocyte common antigen (LCA), CD46/membrane cofactor protein (MCP), CD52/CAMPATH-1, CD55/decay accelerating factor (DAF), CD59/protectin, CDC27, CDK4, carcinoembryonic antigen (CEA), c-myc, cyclooxygenase-2 (cox-2), deleted in colorectal cancer gene (DCC), DcR3, E6/E7, CGFR, EMBP, Dna78, farnesyl transferase, fibroblast growth factor-8a (FGF8a), fibroblast growth factor-8b (FGF8b), FLK-1/KDR, folic acid receptor, G250, G melanoma antigen gene family (GAGE-family), gastrin 17, gastrin-releasing hormone, ganglioside 2 (GD2)/ganglioside 3 (GD3)/ganglioside-monosialic acid-2 (GM2), gonadotropin releasing hormone (GnRH), UDP-GlcNAc:$R_1$Man(α1-6)$R_2$ [GlcNAc to Man(α1-6)] β1,6-N-acetylglucosaminyltransferase V (GnT V), GP1, gp100/Pmel17, gp-100-in4, gp15, gp75/tyrosine-related protein-1 (gp75/TRP-1), human chorionic gonadotropin (hCG), heparanase, Her2/neu, human mammary tumor virus (HMTV), 70 kiloDalton heat-shock protein (HSP70), human telomerase reverse transcriptase (hTERT), insulin-like growth factor receptor-1 (IGFR-1), interleukin-13 receptor (IL-13R), inducible nitric oxide synthase (iNOS), Ki67, KIAA0205, K-ras, H-ras, N-ras, KSA, LKLR-FUT, melanoma antigen-encoding family (MAGE-family, including at least MAGE-1, MAGE-2, MAGE-3, and MAGE-4), mammaglobin, MAP17, Melan-A/melanoma antigen recognized by T-cells-1 (MART-1), mesothelin, MIC A/B, MT-MMPs, mucin (e.g., MUC1), testes-specific antigen NY-ESO-1, osteonectin, p15, P170/MDR1, p53, p97/melanotransferrin, PAI-1, platelet-derived growth factor (PDGF), μPA, PRAME, probasin, progenipoietin, prostate-specific antigen (PSA), prostate-specific membrane antigen (PSMA), RAGE-1, Rb, RCAS1, mutated Ras, SART-1, SSX-family, STAT3, STn, TAG-72, transforming growth factor-alpha (TGF-α), transforming growth factor-beta (TGF-β), Thymosin-beta-15, tumor necrosis factor-alpha (TNF-α), TP1, TRP-2, tyrosinase, vascular endothelial growth factor (VEGF), ZAG, p16INK4, and glutathione-S-transferase (GST), as well as modified versions thereof (e.g., CEA-6D).

In the case of a viral vector, the nucleic acid encoding the peptide, as well as any other exogenous gene(s), preferably are inserted into a site or region (insertion region) in the vector (e.g., poxvirus) that does not affect virus viability of the resultant recombinant virus. Such regions can be readily identified by testing segments of virus DNA for regions that allow recombinant formation without seriously affecting virus viability of the recombinant virus.

The thymidine kinase (TK) gene is an insertion region that can readily be used and is present in many viruses. In particular, the TK gene has been found in all examined poxvirus genomes. Additional suitable insertion sites are described in International Patent Application Publication WO 2005/048957. For example, in fowlpox, insertion regions include, but are not limited to, the BamHI J fragment, EcoRI-HindIII fragment, BamHI fragment, EcoRV-HindIII fragment, long unique sequence (LUS) insertion sites (e.g., FPV006/FPV007 and FPV254/FPV255), FP14 insertion site (FPV060/FPV061), and 43K insertion site (FPV107/FPV108). In vaccinia, insertion sites include, but are not limited to, 44/45, 49/50, and 124/125.

When the vector is a recombinant fowlpox virus comprising a nucleic acid encoding the peptide and/or other exogenous gene(s) (e.g., encoding one or more immunostimulatory/regulatory molecules), the nucleic acid encoding the peptide can be inserted in one region (e.g., the FP14 region), and the exogenous gene(s) can be inserted in another region (e.g., the BamHI J region).

The inventive vector can include suitable promoters and regulatory elements, such as a transcriptional regulatory element or an enhancer. Suitable promoters include the SV40 early promoter, an RSV promoter, the retrovirus LTR, the adenovirus major late promoter, the human CMV immediate early I promoter, and various poxvirus promoters, such as the Pr7.5K promoter, 30K promoter, 40K promoter, 13 promoter, Prs promoter, PrsSynIIm promoter, PrLE1 promoter, synthetic early/late (sE/L) promoter, HH promoter, 11K promoter, and Pi promoter. While the promoters typically will be constitutive promoters, inducible promoters also can be used in the inventive vectors. Such inducible systems allow regulation of gene expression.

In one embodiment of the invention, a cell comprising (1) the peptide or polypeptide, (2) a nucleic acid molecule encoding the peptide or polypeptide, and/or (3) a vector comprising the nucleic acid molecule also is provided herein. Suitable cells include prokaryotic and eukaryotic cells, e.g., mammalian cells, yeast, fungi other than yeast, and bacteria (such as *E. coli*). The cell can be used in vitro, such as for research or for production of the peptide or polypeptide, or the cell can be used in vivo. In one embodiment, the cell is a yeast cell, which may be used to provide a yeast vehicle component of the yeast-based immunotherapy composition as described herein. In another embodiment, the cell can be a peptide-pulsed antigen presenting cell. Suitable antigen presenting cells include, but are not limited to, dendritic cells, B lymphocytes, monocytes, macrophages, and the like.

In one embodiment, the cell is dendritic cell. Dendritic cells of different maturation stages can be isolated based on the cell surface expression markers. For example, mature dendritic cells are less able to capture new proteins for presentation but are much better at stimulating resting T cells to grow and differentiate. Thus, mature dendritic cells can be of importance. Mature dendritic cells can be identified by their change in morphology and by the presence of various markers. Such markers include, but are not limited to, cell surface markers such as B7.1, B7.2, CD40, CD11, CD83, and MHC class II. Alternatively, maturation can be identified by observing or measuring the production of pro-inflammatory cytokines.

Dendritic cells can be collected and analyzed using typical cytofluorography and cell sorting techniques and devices, such as a fluorescence-activated cell sorter (FACS). Antibodies specific to cell surface antigens of different stages of dendritic cell maturation are commercially available.

The peptide, polypeptide, nucleic acid, vector, or cell can be isolated. The term "isolated" as used herein encompasses compounds or compositions that have been removed from a biological environment (e.g., a cell, tissue, culture medium, body fluid, etc.) or otherwise increased in purity to any degree (e.g., isolated from a synthesis medium). Isolated compounds and compositions, thus, can be synthetic or naturally produced.

The peptide, polypeptide, nucleic acid, vector, or cell can be formulated as a composition (e.g., pharmaceutical composition) comprising the peptide, polypeptide, nucleic acid, vector, or cell and a carrier (e.g., a pharmaceutically or physiologically acceptable carrier). Furthermore, the peptide, polypeptide, nucleic acid, vector, cell, or composition of the invention can be used in the methods described herein alone or as part of a pharmaceutical formulation.

The composition (e.g., pharmaceutical composition) can comprise more than one peptide, polypeptide, nucleic acid, vector, or cell of the invention. Vectors and compositions of the invention can further include or can be administered with (concurrently, sequentially, or intermittently with) any other agents or compositions or protocols that are useful for inhibiting HPV infection and/or preventing or treating cancer or any compounds that treat or ameliorate any symptom of cancer, and particularly cancers associated with HPV. For example, the composition can comprise one or more other pharmaceutically active agents or drugs. Examples of such other pharmaceutically active agents or drugs that may be suitable for use in the pharmaceutical composition include anticancer agents (e.g., chemotherapeutic or radiotherapeutic agents), antimetabolites, hormones, hormone antagonists, antibiotics, antiviral drugs, antifungal drugs, cyclophosphamide, and combinations thereof. Suitable anticancer agents include, without limitation, alkylating agents, folate antagonists, purine antagonists, pyrimidine antagonists, spindle poisons, topoisomerase inhibitors, apoptosis inducing agents, angiogenesis inhibitors, podophyllotoxins, nitrosoureas, cisplatin, carboplatin, interferon, asparginase, tamoxifen, leuprolide, flutamide, megestrol, mitomycin, bleomycin, doxorubicin, irinotecan, taxol, geldanamycin (e.g., 17-AAG), and various anti-cancer peptides and antibodies known in the art.

Exemplary alkylating agents include, but are not limited to, nitrogen mustards (e.g., mechlorethamine, cyclophosphamide, melphalan, uracil mustard, or chlorambucil), alkyl sulfonates (e.g., busulfan), nitrosoureas (e.g., carmustine, lomustine, semustine, streptozocin, or dacarbazine). Exemplary antimetabolites include, but are not limited to, folic acid analogs (e.g., methotrexate), pyrimidine analogs (e.g., 5-fluorouracil (5-FU) or cytarabine), and purine analogs (e.g., mercaptopurine or thioguanine). Exemplary hormones and hormone antagonists include, but are not limited to, adrenocorticosteroids (e.g., prednisone), progestins (e.g., hydroxyprogesterone caproate, medroxyprogesterone acetate, and magestrol acetate), estrogens (e.g., diethylstilbestrol and ethinyl estradiol), antiestrogens (e.g., tamoxifen), and androgens (e.g., testosterone proprionate and fluoxymesterone). Other exemplary agents include, but are not limited to, *vinca* alkaloids (e.g., vinblastine, vincristine, or vindesine), epipodophyllotoxins (e.g., etoposide or teniposide), antibiotics (e.g., dactinomycin, daunorubicin, doxorubicin, bleomycin, plicamycin, or mitocycin C), enzymes (e.g., L-asparaginase), platinum coordination complexes (e.g., cis-diamine-dichloroplatinum II also known as cisplatin), substituted ureas (e.g., hydroxyurea), methyl hydrazine derivatives (e.g., procarbazine), and adrenocortical suppressants (e.g., mitotane and aminoglutethimide).

Chemotherapeutics that can be concurrently, sequentially or intermittently administered with the vectors and compositions disclosed herein include Adriamycin, Alkeran, Ara-C, Busul fan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin, Enzalutamide (MDV-3100 or XTANDI™), and calcitriol. Exemplary immunomodulators and/or cytokines include, but are not limited to, AS-101 (Wyeth-Ayerst Labs.), bropirimine (Upjohn), gamma interferon (Genentech), GM-CSF (granulocyte macrophage colony stimulating factor; Genetics Institute), IL-2 (Cetus or Hoffman-LaRoche), human immune globulin (Cutter Biological), IMREG (from Imreg of New Orleans, La.), SK&F 106528, tumor necrosis factor (TNF)-α, and TNF-β.

Other agents, compositions or protocols (e.g., therapeutic protocols) that are useful for the treatment of cancer in conjunction with the peptides, polypeptides (proteins), nucleic acids, vectors, cells, and compositions of the invention include, but are not limited to, surgical resection of a tumor, radiation therapy, allogeneic or autologous stem cell transplantation, T cell adoptive transfer, and/or targeted cancer therapies (e.g., small molecule drugs, biologics, or monoclonal antibody therapies that specifically target molecules involved in tumor growth and progression, including, but not limited to, selective estrogen receptor modulators (SERMs), aromatase inhibitors, tyrosine kinase inhibitors, serine/threonine kinase inhibitors, histone deacetylase (HDAC) inhibitors, retinoid receptor activators, apoptosis stimulators, angiogenesis inhibitors, poly (ADP-ribose) polymerase (PARP) inhibitors, or immunostimulators).

The additional active agent (e.g., anti-viral or chemotherapeutics agent) can be administered before, concurrently with (including simultaneously), alternating with, sequentially, or after administration with the vectors and compositions disclosed herein. In certain embodiments, one or more (e.g., 2, 3, 4, or 5) anti-viral or chemotherapeutic agents is administered in combination with the vectors and compositions disclosed herein.

The additional active agent can be administered alone or in a composition. The additional active agent can be formulated by inclusion in a vector (e.g., plasmid or viral vector), in liposomes (tecemotide, which is also known as STIMUVAX™, L-BLP25, or BLP25 liposome vaccine), or in nanoparticles (e.g., VERSAMUNE™ nanotechnology).

The carrier can be any of those conventionally used and is limited only by physio-chemical considerations, such as solubility and lack of reactivity with the active compound (s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular peptide, polypeptide, nucleic acid, vector, cell, or composition thereof of the invention and other active agents or drugs used, as well as by the particular method used to administer the peptide, polypeptide, nucleic acid, vector, cell, or composition thereof.

The composition additionally or alternatively can comprise one or more immunostimulatory/regulatory molecules. Any suitable immunostimulatory/regulatory molecule can be used, such as interleukin (IL)-2, IL-4, IL-6, IL-12, IL-15, IL-15/IL-15Ra, IL-15/IL-15Ra-Fc, interferon (IFN)-γ, tumor necrosis factor (TNF)-α, B7.1, B7.2, ICAM-1, ICAM-2, LFA-1, LFA-2, LFA-3, CD70, CD-72, RANTES, G-CSF, GM-CSF, OX-40L, 41 BBL, anti-CTLA-4, IDO inhibitor, anti-PDL1, anti-PD1, and combinations thereof. Preferably, the composition comprises a combination of B7.1, ICAM-1, and LFA-3 (also referred to as TRICOM). The one or more immunostimulatory/regulatory molecules can be administered in the form of a vector (e.g., a recombinant viral vector, such as a poxvirus vector) comprising a nucleic acid encoding one or more immunostimulatory/regulatory molecules. For example, the one or more immunostimulatory/regulatory molecules (e.g., IL-12) can be administered in the form of a DNA plasmid with or without chitosan. Alternatively, the one or more immunostimulatory/regulatory molecules can be administered as a protein (e.g., recombinant protein), such as a protein (e.g., recombinant IL-12) admixed with chitosan. One or more immunostimulatory/regulatory molecules also can be administered in combination with, or concurrently with, a yeast-based immunotherapy composition of the invention.

In one embodiment of the invention, the composition comprises a first recombinant vector comprising the nucleic acid encoding the inventive peptide or polypeptide (protein) and second recombinant vector comprising a nucleic acid encoding B7.1, ICAM-1, and LFA-3. In another embodiment, the nucleic acid encoding the inventive peptide or polypeptide (protein) and the nucleic acid encoding B7.1, ICAM-1, and LFA-3 are in the same recombinant vector. The first and/or second vectors additionally can comprise a nucleic acid encoding another tumor associated antigen (e.g., CEA, MUC1, or PSA), a modified version thereof (e.g., CEA-6D), or an epitope thereof.

For example, the recombinant vector can be an avipox vector (e.g., canarypox virus or a fowlpox virus) comprising the nucleic acid encoding the inventive peptide and nucleic acids encoding a B7-1 polypeptide, an ICAM-1 polypeptide, and an LFA-3 polypeptide. Alternatively, the recombinant vector can be an orthopox virus comprising the nucleic acid encoding the inventive peptide and nucleic acids encoding a B7-1 polypeptide, an ICAM-1 polypeptide, and an LFA-3 polypeptide.

The invention provides a method of transducing dendritic cells with the peptide, polypeptide, nucleic acid, vector, cell, or composition thereof, and optionally immunostimulatory/regulatory molecules, such as for example, B7-1, ICAM-1 and LFA-3. In one aspect of the invention, dendritic cells transduced with the peptide, polypeptide, nucleic acid, vector, cell, or composition thereof are administered to the host generate an immune response, such as activation of a cytotoxic T cell response.

The invention provides methods of treating a subject suffering from or susceptible to a HPV-associated tumor and/or enhancing an immune response against a HPV-associated cancer and/or inhibiting a HPV-associated cancer. In a first embodiment, the inventive methods comprise administering a therapeutically effective amount of one or more of the peptide, polypeptide, nucleic acid, vector, cell, or composition thereof to a subject. The inventive peptide, polypeptide, nucleic acid, vector, cell, or composition thereof can be used to prevent the development of a HPV-associated cancer, particularly in an individual at higher risk to develop such cancer than other individuals, or to treat a patient afflicted with a HPV-associated cancer. The inventive peptide, polypeptide, nucleic acid, vector, cell, or composition thereof is useful for preventing emergence of such cancers, arresting progression of such cancers or eliminating such cancers. More particularly, the inventive peptide, polypeptide, nucleic acid, vector, cell, or composition thereof can be used to prevent, inhibit or delay the development of HPV-associated tumors, and/or to prevent, inhibit or delay tumor migration and/or tumor invasion of other tissues (metastases) and/or to generally prevent or inhibit progression of cancer in an individual. The inventive peptide, polypeptide, nucleic acid, vector, cell, or composition thereof can also be used to ameliorate at least one symptom of the cancer, such as by reducing tumor burden in the individual; inhibiting tumor growth in the individual; increasing survival of the individual; and/or preventing, inhibiting, reversing or delaying progression of the cancer in the individual. The inventive peptide, polypeptide, nucleic acid, vector, cell, or composition thereof can be used to treat a subject with any stage HPV-associated cancer.

In a second embodiment, the inventive methods comprise obtaining (by isolating) dendritic cells from a subject, treating the dendritic cells with one or more of the therapeutically effective amount of the peptide, polypeptide, nucleic acid, vector, cell, or composition thereof, and administering the treated dendritic cells to the subject.

In a third embodiment, the inventive methods comprise (a) obtaining (isolating) peripheral blood mononuclear cells (PBMCs) from a subject, (b) isolating dendritic cells from the PBMCs, (c) treating the dendritic cells with one or more of the therapeutically effective amount of the peptide, polypeptide, nucleic acid, vector, cell, or composition thereof ex vivo, (d) activating the PBMCs with the treated dendritic cells ex vivo, and (e) administering the activated PBMCs to the subject.

In a fourth embodiment, the inventive methods comprise a method for inhibiting a HPV-associated cancer in a subject comprising (a) obtaining (isolating) PBMCs from a subject, (b) isolating dendritic cells from the PBMCs, (c) treating the dendritic cells with one or more of the therapeutically effective amount of the peptide, polypeptide, nucleic acid, vector, cell, or composition thereof ex vivo, (d) activating the PBMCs with the treated dendritic cells ex vivo, (e) isolating T lymphocytes from the activated PBMCs ex vivo, and (0 administering the isolated T lymphocytes to the subject.

The invention also provides the use of adoptively transferred T cells stimulated in vitro with one or more of the therapeutically effective amount of the peptide, polypeptide, nucleic acid, vector, cell, or composition thereof to inhibit a HPV-associated cancer in a subject.

Treatment (e.g., inhibiting an HPV infection, inhibiting a HPV-associated cancer and/or enhancing an immune response against a HPV-associated cancer) comprises, but is not limited to, destroying tumor cells, reducing tumor burden, inhibiting tumor growth, reducing the size of the primary tumor, reducing the number of metastatic legions, increasing survival of the individual, delaying, inhibiting, arresting or preventing the onset or development of metastatic cancer (such as by delaying, inhibiting, arresting or preventing the onset of development of tumor migration and/or tumor invasion of tissues outside of primary cancer and/or other processes associated with metastatic progression of cancer), delaying or arresting primary cancer progression, improving immune responses against the tumor, improving long term memory immune responses against the tumor antigens, and/or improving the general health of the individual. It will be appreciated that tumor cell death can occur without a substantial decrease in tumor size due to, for instance, the presence of supporting cells, vascularization, fibrous matrices, etc. Accordingly, while reduction in tumor size is preferred, it is not required in the treatment of cancer.

The HPV-associated cancer can be any cancer associated with HPV infection, including, but not limited to, cervical, anal, and head and neck cancers.

The peptide, polypeptide, nucleic acid, vector, cell, or composition thereof can be administered to the subject by any method. For example, the peptide, polypeptide, or nucleic acid encoding the peptide or polypeptide (e.g., as a vector) can be introduced into a cell (e.g., in a host) by any of various techniques, such as by contacting the cell with the peptide, polypeptide, the nucleic acid, or a composition comprising the nucleic acid as part of a construct, as described herein, that enables the delivery and expression of the nucleic acid. Specific protocols for introducing and expressing nucleic acids in cells are known in the art (see, e.g., Sambrook et al. (eds.), supra; and Ausubel et al., supra).

Suitable methods of administering peptides, polypeptides (proteins), nucleic acids, vectors, cells, and compositions to hosts (subjects) are known in the art. The host (subject or individual) can be any suitable host, such as a mammal (e.g., a rodent, such as a mouse, rat, hamster, or guinea pig, rabbit, cat, dog, pig, goat, cow, horse, primate, or human).

For example, the peptide, polypeptide, nucleic acid, or vector (e.g., recombinant poxvirus) can be administered to a host by exposure of tumor cells to the peptide, polypeptide, nucleic acid, or vector ex vivo or by injection of the peptide, polypeptide, nucleic acid, or vector into the host. The peptide, polypeptide, nucleic acid, vector (e.g., recombinant poxvirus) or combination of vectors, cell, and composition can be directly administered (e.g., locally administered) by direct injection into the cancerous lesion or tumor or by topical application (e.g., with a pharmaceutically acceptable carrier).

The peptide, polypeptide, nucleic acid, vector, cell, or composition thereof can be administered alone or in combination with adjuvants, incorporated into liposomes (as described in, e.g., U.S. Pat. Nos. 5,643,599, 5,464,630, 5,059,421, and 4,885,172), incorporated into nanoparticles (e.g., VERSAMUNE™ nanotechnology), administered with cytokines, administered with biological response modifiers (e.g., interferon, interleukin-2 (IL-2), administered colony-stimulating factors (CSF, GM-CSF, and G-CSF), and/or administered other reagents in the art that are known to enhance immune response.

Examples of suitable adjuvants include alum, aluminum salts, aluminum phosphate, aluminum hydroxide, aluminum silica, calcium phosphate, incomplete Freund's adjuvant, saponins, such as QS21 (an immunological adjuvant derived from the bark of the South American tree *Quillaja saponaria Molina*), monophosphoryl lipid A (MLP-A), and RIBI DETOX™ adjuvant.

A particularly preferred adjuvant for use in the invention is the cytokine GM-CSF. GM-CSF has been shown to be an effective vaccine adjuvant because it enhances antigen processing and presentation by dendritic cells. Experimental and clinical studies suggest that recombinant GM-CSF can boost host immunity directed at a variety of immunogens.

GM-CSF can be administered using a viral vector (e.g., poxvirus vector) or as an isolated protein in a pharmaceutical formulation. GM-CSF can be administered to the host before, during, or after the initial administration of the peptide, polypeptide, nucleic acid, vector, cell, or composition thereof to enhance the antigen-specific immune response in the host. For example, recombinant GM-CSF protein can be administered to the host on each day of vaccination with the peptide, polypeptide, nucleic acid, vector, cell, or composition thereof and for each of the following 3 days (i.e. a total of 4 days). Any suitable dose of GM-CSF can be used. For instance, 50-500 μg (e.g., 100 μg, 200 μg, 300 μg, 400 μg, and ranges therebetween) of recombinant GM-CSF can be administered per day. The GM-CSF can be administered by any suitable method (e.g., subcutaneously) and, preferably, is administered at or near the site of the vaccination of a host with the peptide, polypeptide, nucleic acid, vector, cell, or composition thereof.

In one embodiment, the inventive peptide or polypeptide (protein) can be conjugated to helper peptides or to large carrier molecules to enhance the immunogenicity of the peptide or polypeptide. These molecules include, but are not limited to, influenza peptide, tetanus toxoid, tetanus toxoid CD4 epitope, *Pseudomonas* exotoxin A, poly-L-lysine, a lipid tail, endoplasmic reticulum (ER) signal sequence, and the like.

The inventive peptide or polypeptide (protein) also can be conjugated to an immunoglobulin molecule using art-accepted methods. The immunoglobulin molecule can be specific for a surface receptor present on tumor cells, but absent or in very low amounts on normal cells. The immunoglobulin also can be specific for a specific tissue (e.g., breast, ovarian, colon, or prostate tissue). Such a peptide-immunoglobulin conjugate or polypeptide-immunoglobulin conjugate allows for targeting of the peptide to a specific tissue and/or cell.

The peptide, polypeptide, nucleic acid, vector, cell, or composition thereof is administered to a host (e.g., mammal, such as a human) in an amount effective to generate a HPV-associated immune response, preferably a cellular immune response. The efficacy of the peptide, polypeptide, nucleic acid, vector, or cell as an immunogen may be determined by in vivo or in vitro parameters as are known in the art. These parameters include but are not limited to antigen-specific cytotoxicity assays, regression of tumors expressing HPV or HPV epitopes, inhibition of HPV-associated cancer cells, production of cytokines, and the like.

Any suitable dose of the peptide, polypeptide, nucleic acid, vector, or cell or composition thereof can be administered to a host. The appropriate dose will vary depending upon such factors as the host's age, weight, height, sex, general medical condition, previous medical history, disease progression, and tumor burden and can be determined by a clinician. For example, the peptide can be administered in a dose of about 0.05 mg to about 10 mg (e.g., 0.1 mg, 0.5 mg, 1 mg, 2 mg, 3 mg, 4 mg, 5 mg, 6 mg, 7 mg, 8 mg, 9 mg, and ranges therebetween) per vaccination of the host (e.g., mammal, such as a human), and preferably about 0.1 mg to about 5 mg per vaccination. Several doses (e.g., 1, 2, 3, 4, 5, 6, or more) can be provided (e.g., over a period of weeks or months). In one embodiment a dose is provided every month for 3 months.

When the vector is a viral vector, a suitable dose can include about $1\times10^5$ to about $1\times10^{12}$ (e.g., $1\times10^6$, $1\times10^7$, $1\times10^8$, $1\times10^9$, $1\times10^{10}$, $1\times10^{11}$, and ranges therebetween) plaque forming units (pfus), although a lower or higher dose can be administered to a host. For example, about $2\times10^8$ pfus can be administered (e.g., in a volume of about 0.5 mL).

The inventive cells (e.g., cytotoxic T cells) can be administered to a host in a dose of between about $1\times10^5$ and $2\times10^{11}$ (e.g., $1\times10^6$, $1\times10^7$, $1\times10^8$, $1\times10^9$, $1\times10^{10}$, and ranges therebetween) cells per infusion. The cells can be administered in, for example, one to three (e.g., one, two, or three) infusions. In addition to the administration of the cells, the host can be administered a biological response modifier, such as interleukin 2 (IL-2). When the cells to be administered are cytotoxic T cells, the administration of the cytotoxic T cells can be followed by the administration of the peptide, polypeptide, nucleic acid, vector, or composition thereof in order to prime the cytotoxic T cells to further expand the T cell number in vivo.

When the cells to be administered are dendritic cells, the amount of dendritic cells administered to the subject will vary depending on the condition of the subject and should be determined via consideration of all appropriate factors by the practitioner. Preferably, about $1\times10^6$ to about $1\times10^{12}$ (e.g., about $1\times10^7$, about $1\times10^8$, about $1\times10^9$, about $1\times10^{10}$, or about $1\times10^{11}$ including ranges between of any of the cell numbers described herein) dendritic cells are utilized for adult humans. These amounts will vary depending on the age, weight, size, condition, sex of the subject, the type of tumor to be treated, the route of administration, whether the treatment is regional or systemic, and other factors. Those skilled in the art should be readily able to derive appropriate dosages and schedules of administration to suit the specific circumstance and needs of the subject.

The invention provides a method of generating peptide-specific cytotoxic T lymphocytes in vivo, ex vivo, or in vitro by stimulation of lymphocytes with an effective amount of the inventive peptide, polypeptide, nucleic acid, vector, or cell, alone or in a composition with one or more immunostimulatory/regulatory molecules and/or adjuvants or in a liposome formulation. The lymphocytes can be lymphocytes from any suitable source, e.g., peripheral blood, tumor tissues, lymph nodes, and effusions, such as pleural fluid or ascites fluid.

The HPV peptide specific cytotoxic T lymphocytes are immunoreactive with HPV. Preferably, the cytotoxic T lymphocytes inhibit the occurrence of tumor cells and cancer and inhibit the growth of, or kill, HPV-associated tumor cells. The cytotoxic T lymphocytes, in addition to being antigen specific, can be MHC class I restricted. In one embodiment, the cytotoxic T lymphocytes are MHC class 1 HLA-A24 restricted. The cytotoxic T lymphocytes preferably have a $CD8^+$ phenotype.

In one embodiment, lymphocytes are removed from the host and stimulated ex vivo with the peptide, polypeptide, nucleic acid, vector, cell, or composition thereof to generate cytotoxic T lymphocytes. The cytotoxic T lymphocytes can be administered to the host in order to enhance an immune response to cancer, thereby inhibiting the cancer. Accordingly, the invention provides a method of inhibiting cancer in a host comprising (a) obtaining lymphocytes (e.g., from the host), (b) stimulating the lymphocytes with the peptide, polypeptide, nucleic acid, vector, cell, or composition thereof to generate cytotoxic T lymphocytes, and (c) administering the cytotoxic T lymphocytes to the host, wherein the cancer is inhibited.

In another embodiment, lymphocytes within the host are stimulated by administration to the host of the peptide, polypeptide, nucleic acid, vector, cell, or composition thereof to generate cytotoxic T lymphocytes, which cytotoxic T lymphocytes enhance an immune response to cancer, thereby inhibiting the cancer.

The invention includes a prime and boost protocol. In particular, in one embodiment related to peptides, polypeptides, and vectors of the invention, the protocol includes an initial "prime" with a composition comprising one or more recombinant vectors encoding the inventive peptide or polypeptide and optionally one or more immunostimulatory/regulatory molecules and/or other tumor-associated antigens (e.g., CEA, MUC1, or PSA), modified versions thereof, and immunogenic epitopes thereof, followed by one or preferably multiple "boosts" with a composition containing the inventive peptide or polypeptide or one or more poxvirus vectors encoding the inventive peptide or polypeptide and optionally one or more immunostimulatory/regulatory molecules and/or other tumor-associated antigens (e.g., CEA, MUC1, or PSA), modified versions thereof, and immunogenic epitopes thereof.

In this embodiment, the initial priming vaccination can comprise one or more vectors. In one embodiment, a single vector (e.g., poxvirus vector) is used for delivery of the inventive peptide and one or more immunostimulatory/regulatory molecules and/or other tumor-associated antigens (e.g., CEA, MUC1, or PSA), modified versions thereof, and immunogenic epitopes thereof. In another embodiment, two or more vectors (e.g., poxvirus vectors) comprise the priming vaccination, which are administered simultaneously in a single injection.

The boosting vaccinations also can comprise one or more vectors (e.g., poxvirus vectors). In one embodiment, a single vector is used for delivery of the inventive peptide and the one or more immunostimulatory/regulatory molecules and/or other tumor-associated antigens (e.g., CEA, MUC1, or PSA), modified versions thereof, and immunogenic epitopes thereof of the boosting vaccination. In another embodiment, two or more vectors comprise the boosting vaccination, which are administered simultaneously in a single injection.

Different vectors (e.g., poxvirus vectors) can be used to provide a heterologous prime/boost protocol using vectors carrying different sets of therapeutic molecules for inoculations at different time intervals. For example, in one heterologous prime/boost combination, a first orthopox vector composition is used to prime, and a second avipox vector composition is used to boost.

The schedule for administration of the vectors (e.g., poxvirus vectors) typically involves repeated administration of the boosting vector. The boosting vector can be administered 1-3 times (e.g., 1, 2, or 3 times) at any suitable time period (e.g., every 2-4 weeks) for any suitable length of time (e.g., 6-12 weeks for a total of at least 5 to 15 boosting vaccinations). For example, the primary vaccination can comprise a recombinant vaccinia or MVA vector followed by multiple booster vaccinations with an avipox vector. In a particular embodiment, the host receives one vaccination with the priming vector, followed every 2 weeks thereafter with the boosting vector for 6 boosts, followed by every 4 weeks thereafter with the boosting vector, and continuing with the boosting vector for a period of time dependent on disease progression.

The invention further provides a kit that, in one embodiment, has at least a first recombinant vector (e.g., poxvirus vector) that has incorporated into its genome or portion thereof a nucleic acid encoding the inventive peptide or polypeptide in a pharmaceutically acceptable carrier. The first recombinant vector (e.g., poxvirus vectors) also can comprise one or more nucleic acids encoding one or more immunostimulatory/regulatory molecules and/or other tumor-associated antigens (e.g., CEA, MUC1, or PSA), modified versions thereof, and immunogenic epitopes thereof in addition to the first recombinant vector, the kit can have a second recombinant vector that comprises one or more nucleic acids encoding one or more immunostimulatory/regulatory molecules and/or other tumor-associated antigens (e.g., CEA, MUC1, or PSA), modified versions thereof, and immunogenic epitopes thereof in a pharmaceutically acceptable carrier. The kit further provides containers, injection needles, and instructions on how to use the kit. In another embodiment, the kit further provides an adjuvant such as GM-CSF and/or instructions for use of a commercially available adjuvant with the kit components.

Accordingly, the invention provides a method of inducing an immune response against an HPV-associated cancer in a subject comprising (a) administering to the subject a first vector (e.g., viral vector, such as a poxviral vector) comprising a nucleic acid encoding the amino acid sequence of SEQ ID NO: 1, SEQ ID NO: 2, or SEQ ID NO: 3 and (b) administering to the subject a second vector (e.g., viral vector, such as a poxviral vector) comprising a nucleic acid encoding the amino acid sequence of SEQ ID NO: 1, SEQ ID NO: 2, or SEQ ID NO: 3. In one embodiment, the nucleic acid encoding the amino acid sequence of SEQ ID NO: 1, SEQ ID NO: 2, or SEQ ID NO: 3 is a nucleic acid encoding an HPV (e.g., HPV-16) protein comprising the amino acid sequence of SEQ ID NO: 1, SEQ ID NO: 2, or SEQ ID NO: 3. In particular, the HPV protein can be a HPV (e.g., HPV-16) E6 protein or HPV (e.g., HPV-16) E7 protein.

As discussed above, the peptide, polypeptide, nucleic acid, vector, cell, or composition thereof can be administered to a host by various routes including, but not limited to, subcutaneous, intramuscular, intradermal, intraperitoneal, intravenous, and intratumoral. When multiple administrations are given, the administrations can be at one or more sites in a host and a single dose can be administered by dividing the single dose into equal portions for administration at one, two, three, four or more sites on the individual.

Administration of the peptide, polypeptide, nucleic acid, vector, cell, or composition thereof can be "prophylactic" or "therapeutic." When provided prophylactically, the peptide, polypeptide, nucleic acid, vector, cell, or composition thereof is provided in advance of tumor formation, or the detection of the development of HPV-associated tumors, with the goal of preventing, inhibiting or delaying the development of HPV-associated tumors; and/or preventing, inhibiting or delaying metastases of such tumors and/or generally preventing or inhibiting progression of cancer in an individual, and generally to allow or improve the ability of the host's immune system to fight against a tumor that the host is susceptible of developing. The prophylactic administration of the peptide, polypeptide, nucleic acid, vector, cell, or composition thereof prevents, ameliorates, or delays the HPV-associated cancer. When provided therapeutically, the peptide, polypeptide, nucleic acid, vector, cell, or composition thereof is provided at or after the diagnosis of the M HPV-associated cancer, with the goal of ameliorating the cancer, such as by reducing tumor burden in the individual; inhibiting tumor growth in the individual; increasing survival of the individual; and/or preventing, inhibiting, reversing or delaying progression of the cancer in the individual.

When the host has already been diagnosed with the HPV-associated cancer or metastatic cancer, the peptide, polypeptide, nucleic acid, vector, cell, or composition thereof can be administered in conjunction with other therapeutic treatments such as chemotherapy, surgical resection of a tumor, treatment with targeted cancer therapy, allogeneic or autologous stem cell transplantation, T cell adoptive transfer, other immunotherapies, and/or radiation.

In a preferred embodiment, the administration of the peptide, polypeptide, nucleic acid, vector, cell, or composition thereof to a host results in a host cell expressing the inventive peptide and optionally one or more immunostimulatory/regulatory molecules and/or other tumor-associated antigens (e.g., CEA, MUC1, or PSA), modified versions thereof, and immunogenic epitopes thereof that were co-administered. The inventive peptide (i.e., HPV agonist epitope) can be expressed at the cell surface of the infected host cell. The one or more immunostimulatory/regulatory molecules and/or other tumor-associated antigens (e.g., CEA, MUC1, or PSA), modified versions thereof, and immunogenic epitopes thereof can be expressed at the cell surface or may be actively secreted by the host cell. The expression of both the HPV agonist peptide and the immunostimulatory/regulatory molecule provides the necessary MHC restricted peptide to specific T cells and the appropriate signal to the T cells to aid in antigen recognition and proliferation or clonal expansion of antigen specific T cells. The overall result is an upregulation of the immune system. Preferably, the upregulation of the immune response is an increase in antigen specific T-helper lymphocytes and/or cytotoxic lymphocytes, which are able to kill or inhibit the growth of a cancer (e.g., cervical, anal, and head and neck cancer) cell.

There are a variety of suitable formulations of the pharmaceutical composition for the inventive methods. The following formulations for parenteral, subcutaneous, intravenous, intramuscular, and intraperitoneal administration are exemplary and are in no way limiting. One skilled in the art will appreciate that these routes of administering the peptide, polypeptide, nucleic acid, vector, cell, or composition of the invention are known, and, although more than one route can be used to administer a particular compound, a particular route can provide a more immediate and more effective response than another route.

Injectable formulations are among those formulations that are preferred in accordance with the present invention. The requirements for effective pharmaceutical carriers for injectable compositions are well-known to those of ordinary skill in the art (see, e.g., Pharmaceutics and Pharmacy Practice, J.B. Lippincott Company, Philadelphia, Pa., Banker and Chalmers, eds., pages 238-250 (1982), and ASHP Handbook on Injectable Drugs, Toissel, 4th ed., pages 622-630 (1986)).

Formulations suitable for parenteral administration include aqueous and non-aqueous, isotonic sterile injection solutions, which can contain anti-oxidants, buffers, bacteriostats, and Solutes that render the formulation isotonic with the blood of the intended recipient, and aqueous and non-aqueous sterile suspensions that can include suspending agents, solubilizers, thickening agents, stabilizers, and preservatives. The peptide, polypeptide, nucleic acid, vector, cell, or composition thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethylene glycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, and synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

The following examples further illustrate the invention but, of course, should not be construed as in any way limiting its scope.

EXAMPLE 1

This example demonstrates the binding of HPV-16 E6 and E7 peptides and analogue peptides to HLA-A2 molecules.

Six potential agonist epitopes were identified: 3 agonist epitopes in the E6 HPV region (designated E6-A1, E6-A2, and E6-A3) and 3 agonist epitopes in the E7 HPV region (designated E7-A1, E7A2, and E7-A3). Binding to HLA-A2 was tested and the results summarized in Table 1.

TABLE 1

| E6 | Sequence | Position | BIMAS | T2A2 Binding |
|---|---|---|---|---|
| E6-1 | KLPQLCTEL (SEQ ID NO: 4) | 11-19 | 74.768 | 853 |
| E6-A1 | KLPQLCTE<u>V</u> (SEQ ID NO: 1) (L19V) | | 243.432 | 1,335 |
| E6-2 | KISEYRHYC (SEQ ID NO: 5) | 72-80 | 53.914 | 761 |
| E6-A2 | KISEYRHY<u>V</u> (SEQ ID NO: 6) (C80V) | | 754.791 | 877 |

TABLE 1-continued

| | | | | |
|---|---|---|---|---|
| E6-3 | QQYNKPLCDL (SEQ ID NO: 7) | 90-99 | 15.941 | 1,020 |
| E6-A3 | Q**L**YNKPLCD**V** (SEQ ID NO: 2) (Q91L/L99V) | | 511.903 | 1,280 |
| E7 | | | | |
| E7-1 | YMLDLQPET (SEQ ID NO: 8) | 11-19 | 375.567 | 1,105 |
| E7-A1 | YMLDLQPE**V** (SEQ ID NO: 9) (T19V) | | 3505.289 | 1,171 |
| E7-2 | TLHEYMLDL (SEQ ID NO: 10) | 7-15 | 201.447 | 975 |
| E7-A2 | TLHEYMLD**V** (SEQ ID NO: 11) (L15V) | | 655.875 | 1,529 |
| E7-3 | RTLEDLLMGT (SEQ ID NO: 12) | 77-86 | 3.611 | 839 |
| E7-A3 | R**T**LEDLLMG**V** (SEQ ID NO: 3) (T86V) | | 2426.739 | 1,263 |
| NEG | Negative control | | | 812 |
| TP2a | Positive control | | | 1,540 |

HLA-A2 binding was strongest with agonists E6-A1, E7-A2, and E7-A3.

EXAMPLE 2

This example demonstrates the production of IFN-γ by CTL stimulated by autologous B cells pulsed with corresponding E6 peptides.

Autologous B cells were pulsed with each native and agonist E6 peptides to stimulate production of interferon by T cells. The results are summarized in Table 2.

TABLE 2

| | HPV-16 E6 peptide | IFN-γ (pg/ml) |
|---|---|---|
| T-1066 E6-1 | KLPQLCTEL (SEQ ID NO: 4) | 264 |
| T-1066 E6-1 | NO | <15.6 |
| T-1066 E6-A1 | KLPQLCTE**V** (SEQ ID NO: 1) (L19V) | 699 |
| T-1066 E6-A1 | NO | <15.6 |
| T-1066 E6-2 | KISEYRHYC (SEQ ID NO: 5) | 455 |
| T-1066 E6-2 | NO | <15.6 |
| T-1066 E6-A2 | KISEYRHY**V** (SEQ ID NO: 6) (C80V) | 172 |
| T-1066 E6-A2 | NO | <15.6 |
| T-1066 E6-3 | QQYNKPLCDL (SEQ ID NO: 7) | 338 |
| T-1066 E6-3 | NO | 121 |
| T-1066 E6-A3 | Q**L**YNKPLCD**V** (SEQ ID NO: 2) (Q91L/L99V) | 653 |
| T-1066 E6-A3 | NO | <15.6 |

The best interferon production was seen by agonist E6-A1. Native epitope E6-A2 actually produced more interferon than the agonist counterpart.

EXAMPLE 3

This example demonstrates the production of IFN-γ by CTL stimulated by autologous B cells pulsed with corresponding E7 peptides.

Autologous B cells were pulsed with each native and agonist E7 peptides to stimulate production of interferon by T cells. The results are summarized in Table 3.

TABLE 3

| | HPV-16 E7 peptide | IFN-γ (pg/ml) |
|---|---|---|
| T-1066 E7-1 | YMLDLQPET (SEQ ID NO: 8) | 247 |
| T-1066 E7-1 | NO | 155.6 |
| T-1066 E7-A1 | YMLDLQPEV (SEQ ID NO: 9) (T19V) | 230 |
| T-1066 E7-A1 | NO | <15.6 |
| T-1066 E7-2 | TLHEYMLDL (SEQ ID NO: 10) | 475 |
| T-1066 E7-2 | NO | 95.6 |
| T-1066 E7-A2 | TLHEYMLDV (SEQ ID NO: 11) (L15V) | 95.3 |
| T-1066 E7-A2 | NO | <15.6 |
| T-1066 E7-3 | RTLEDLLMGT (SEQ ID NO: 12) | 338 |
| T-1066 E7-3 | NO | <15.6 |
| T-1066 E7-A3 | RTLEDLLMGV (SEQ ID NO: 3) (T86V) | 840 |
| T-1066 E7-A3 | NO | <15.6 |

The best interferon production was seen by agonist E7-A3. While there was good binding of HLA-A2 of agonist E7-A2 (see Example 1), interferon production was low. Native epitope E7-A2 actually produced more interferon than the agonist counterpart.

EXAMPLE 4

This example demonstrates that HLA-A2 restricted HPV E6 and E7 specific CTLs lyse HLA-A2 positive and HPV16 E6 and E7 positive tumor cells.

HPV-specific T cells were generated using infection of dendritic cells (DCs) with Ad-HPV followed by stimulation of the T cells with each agonist and native peptide. In particular, DCs were infected with Ad5 HPV at 20,000 MOI. Infected DCs were used to generate specific CTLs using autologous PBMC. Autologous DCs were used as APCs for three in vitro stimulations (IVS). Autologous peptide-pulsed B cells were used to re-stimulate antigen-specific CTLs for two additional IVS. CTLs were used at IVS5.

Results are expressed in % specific lysis (SD). Effector-to-target ratio used was 25:1. CTLs were established from a normal HLA-A2 donor. CaSki is a cervical carcinoma cell line (HPV16 E6 and E7 positive HLA-A2 positive). ASPC-1 is a pancreatic cancer cell line (HPV16 E6 and E7 negative HLA-A2 negative).

TABLE 4

| | AA Position | HPV-16 peptide | CaSki (HLA-A2$^{+}$ HPV E6$^{+}$ and E7$^{+}$ | ASPC-1 (HLA-A2$^{neg}$ HPV E6$^{neg}$ and E7$^{neg}$) |
|---|---|---|---|---|
| T-1066 E6-1 | E6 11-19 | KLPQLCTEL (SEQ ID NO: 4) | 34.1 (3.6) | 2.4 (0.6) |
| T-1066 E6-A1 | E6 11-19 | KLPQLCTEV (SEQ ID NO: 1) (L19V) | 70.8 (10.7) | -0.2 (6.6) |
| T-1066 E6-2 | E6 72-80 | KISEYRHYC (SEQ ID NO: 5) | 45.1 (2.8) | 0.5 (0.7) |
| T-1066 E6-A2 | E6 72-80 | KISEYRHYV (SEQ ID NO: 6) (C80V) | 24.2 (1.2) | 0.2 (0.5) |
| T-1066 E6-3 | E6 90-99 | QQYNKPLCDL (SEQ ID NO: 7) | 38.1 (3.3) | 0.6 (0.2) |
| T-1066 E6-A3 | E6 90-99 | QLYNKPLCDV (SEQ ID NO: 2) (Q91L/L99V) | 49.1 (11.9) | 0.3 (0.9) |
| T-1066 E7-1 | E7 11-19 | YMLDLQPET (SEQ ID NO: 8) | 39.8 (1.7) | 0.4 (0.3) |
| T-1066 E7-A1 (T19V) | E7 11-19 | YMLDLQPEV (SEQ ID NO: 9) | 27.8 (3.6) | 0.9 (0.6) |
| T-1066 E7-2 | E7 7-15 | TLHEYMLDL (SEQ ID NO: 10) | 59.2 (5.3) | 0.1 (1.0) |
| T-1066 E7-A2 | E7 7-15 | TLHEYMLDV (SEQ ID NO: 11) (L15V) | 41.9 (4.1) | 0.6 (1.3) |
| T-1066 E7-3 | E7 77-86 | RTLEDLLMGT (SEQ ID NO: 12) | 49.6 (8.7) | 0.5 (0.1) |
| T-1066 E7-A3 | E7 77-86 | RTLEDLLMGV (SEQ ID NO: 3) (T86V) | 54.5 (7.3) | 0.6 (0.1) |

Enhanced lysis of CaSki cervical carcinoma cells was seen by T cells generated with agonist epitopes E6-A1, E6-A3, and E7-A3 compared to lysis by T cells generated with the native epitope counterpart. The CaSki tumor cells expressed the native HPV epitopes. No lysis was observed using any epitope with the ASPC1 control cell line.

EXAMPLE 5

This example demonstrates that HLA-A2 restricted HPV E6 and E7 specific CTLs lyse HLA-A2 positive head and neck squamous cell carcinoma cells.

HPV-specific T cells were generated using infection of dendritic cells (DCs) with Ad-HPV followed by stimulation of the T cells with each agonist and native peptide. In particular, DCs were infected with Ad5 HPV at 20,000 MOI. Infected DCs were used to generate specific CTLs using autologous PBMC. Autologous DCs were used as APCs for three in vitro stimulations (IVS). Autologous peptide-pulsed B cells were used to re-stimulate antigen-specific CTLs for two additional IVS. CTLs were used at IVS5.

Results are expressed in % specific lysis (SD). Effector-to-target ratio used was 25:1. CTLs were established from a normal HLA-A2 donor. HN-4 and HN-12 cells are head and neck squamous carcinoma cell lines (HLA-A2 positive). ASPC-1 is a pancreatic cancer cell line (HPV16 E6 and E7 negative HLA-A2 negative).

TABLE 6

| DCs Infected | HPV-Specific T Cell Lines | | | | | |
|---|---|---|---|---|---|---|
| With: | T-E6-1 | T-E6-A1 | T-E6-3 | T-E6-A3 | T-E7-3 | T-E7-A3 |
| Ad5 [E1, E2b]-HPV (20,000 MOI) | 114 | 683 | 135 | 452 | 560 | 931 |
| Ad5 [E1, E2b]-Null (20,000 MOI) | <0.73 | 1.0 | 58.5 | 0.78 | 70.8 | <0.73 |
| DCs only | 2.17 | <0.73 | <0.73 | 8.06 | 4.24 | <0.73 |
| No DCs | <0.73 | 0.89 | <0.73 | 0.9 | <0.73 | <0.73 |

Human DCs infected with Ad-5[E1,E2b$^{neg}$]HPV are able to activate the T cells directed against each of the E6-A1, E6-A3, and E7-A3 agonist epitopes. No activation was seen when DCs were infected with the control Ad-5 vector.

TABLE 5

| Peptide | AA Position | Sequence | Tumor Cells HN-4 | HN-12 | ASPC-1 |
|---|---|---|---|---|---|
| T-1066 E6-1 | E6 11-19 | KLPQLCTEL (SEQ ID NO: 4) | 21.2 (4.4) | 16.5 (1.7) | 0.3 (0.9) |
| T-1066 E6-A1 | E6 11-19 | KLPQLCTEV (SEQ ID NO: 1) (L19V) | 46.2 (1.1) | 49.4 (3.1) | 0.2 (0.9) |
| T-1066 E6-3 | E6 90-99 | QQYNKPLCDL (SEQ ID NO: 7) | 7.0 (0.4) | 10.2 (3.8) | -1.1 (0.7) |
| T-1066 E6-A3 | E6 90-99 | QLYNKPLCDV (SEQ ID NO: 2) (Q91L/L99V) | 30.6 (5.3) | 38.4 (7.5) | 0.5 (0.8) |
| T-1066 E7-3 | E7 77-86 | RTLEDLLMGT (SEQ ID NO: 12) | 25.8 (3.5) | 34.6 (3.9) | 1.1 (0.7) |
| T-1066 E7-A3 | E7 77-86 | RTLEDLLMGV (SEQ ID NO: 3) (T86V) | 40.2 (1.8) | 41.9 (2.9) | 0.6 (0.7) |

Similar results were observed in the lysis of two HPV positive head and neck squamous cell carcinoma cell lines as in Example 4. In each case, the T cell T cells generated with agonist epitopes E6-A1, E6-A3, and E7-A3 showed more lysis of both cell lines that their native counterparts. The tumor cells expressed the native HPV epitopes. No lysis was observed using any epitope with the ASPC1 control cell line.

EXAMPLE 6

This example demonstrates that infection of human dendritic cells (from a HLA-A2 donor) with recombinant serotype 5 adenovirus-HPV (Ad5-HPV) vectors encoding transgenes can activate HPV-specific T cell lines to produce IFN-γ.

Human DC (6 day culture in IL-4 and GM-CSF) were infected with Ad5 [E1,E2b]-HPV vector and Ad5 [E1,E2b]-Null at $1\times10^5$/well (24-well plate) in 0.5 ml of AIM-V. Ad5 vectors were used at 20,000 MOI for 1 hour and then 1.5 ml of AIM-V were added to each well. Infected DCs were incubated for 48 hours and then washed and used for stimulation of human antigen-specific T cells. Results are expressed in pg of IFN-γ per $5\times10^5$ T cells/ml. DC only=<0.73 pg/ml.

EXAMPLE 7

This example provides a summary of comparisons of the E6 and E7 analogue peptides and the native epitopes.

+ denotes a greater level than the native epitope; = denotes the same level as the native epitope; and – denotes a lower level than the native epitope.

TABLE 7

| | Algorithm | A2 Binding | IFN-γ | Lysis |
|---|---|---|---|---|
| E6A1 | +++ | ++ | +++ | +++ |
| E6A2 | +++ | = | – | – |
| E6A3 | +++ | + | ++ | + |
| E7A1 | +++ | = | = | – |
| E7A2 | +++ | ++ | – | – |
| E7A3 | +++ | ++ | +++ | + |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A peptide comprising the amino acid sequence of SEQ ID NO: 2 or SEQ ID NO: 3, wherein the peptide has no more than 20 amino acid residues.

2. The peptide of claim 1, wherein the peptide consists of SEQ ID NO: 2 or SEQ ID NO: 3.

3. A nucleic acid encoding the peptide of claim 1.

4. A vector comprising the nucleic acid of claim 3.

5. A vector comprising a nucleic acid that encodes at least two peptides of claim 1.

6. A cell comprising (i) one or more of the peptides of claim 1, (ii) one or more nucleic acids encoding (i), or (iii) one or more vectors comprising (ii).

7. The cell of claim 6, wherein the cell is human.

8. The cell of claim 6, wherein the cell is an antigen presenting cell or tumor cell.

9. A composition comprising:

(a) (i) one or more of the peptides of claim 1, (ii) one or more nucleic acids encoding (i), (iii) one or more vectors comprising (ii), or (iv) one or more cells comprising (i)-(iii), and (b) a pharmaceutically acceptable carrier.

10. The composition of claim 9, further comprising an immunostimulatory/regulatory molecule.

11. The composition of claim 10, wherein the immunostimulatory/regulatory molecule is selected from the group consisting of interleukin (IL)-2, IL-4, IL-6, IL-12, IL-15, IL-15/IL15Ra, IL-15/IL-15Ra-Fc, interferon (IFN)-y, tumor necrosis factor (TNF)-a, B7.1, B7.2, ICAM-1, LFA-3, CD70, RANTES, G-CSF, OX-40L, 41 BBL, anti-CTLA-4, IDO inhibitor, anti-PDL1, anti-PD1, and combinations thereof.

12. The composition of claim 10, wherein the immunostimulatory/regulatory molecule is selected from the group consisting of (i) a plasmid encoding IL-12 complexed with chitosan and (ii) recombinant IL-12 admixed with chitosan.

13. The composition of claim 9, further comprising a chemotherapeutic drug, radioactive agent, antimetabolite, hormone, hormone antagonist, antibiotic, antiviral drug, antifungal drug, cyclophosphamide, or a combination thereof.

14. The composition of claim 9, further comprising an alkylating agent, folate antagonist, purine antagonist, pyrimidine antagonist, spindle poison, topoisomerase inhibitor, apoptosis inducing agent, angiogenesis inhibitor, podophyllotoxin, nitrosourea, cisplatin, carboplatin, interferon, asparginase, tamoxifen, leuprolide, flutamide, megestrol, mitomycin, bleomycin, doxorubicin, irinotecan, taxol, geldanamycin, or a combination thereof.

15. The composition of claim 9, further comprising Adriamycin, Alkeran, Ara-C, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol, Velban, Vincristine, VP-16, Gemcitabine, Herceptin, Irinotecan, Leustatin, Navelbine, Rituxan STI-571, Taxotere, Topotecan, Capecitabine, Zevelin, Enzalutamide, calcitriol, or a combination thereof.

16. The composition of claim 9, further comprising one or more adjuvants.

17. The composition of claim 16, wherein one or more adjuvants is selected from the group consisting of alum, aluminum salts, aluminum phosphate, aluminum hydroxide, aluminum silica, calcium phosphate, incomplete Freund's adjuvant, QS21, MPL-A, RIBI DETOX™, and combinations thereof.

18. The composition of claim 9, further comprising granulocyte monocyte colony stimulating factor (GM-CSF).

19. The composition of claim 9, further comprising liposomes.

20. A method of inhibiting HPV infection in a subject comprising administering a therapeutically effective amount of the composition of claim 9 to the subject, wherein HPV infection in the subject is inhibited.

21. A method of enhancing an immune response against an HPV-associated cancer in a subject comprising administering a therapeutically effective amount of the composition of claim 9 to the subject, wherein the immune response in the subject is enhanced.

22. A method of inhibiting an HPV-associated cancer in a subject comprising:

(a) obtaining lymphocytes from the subject, (b) stimulating the lymphocytes with the composition of claim 9 to generate cytotoxic T lymphocytes ex vivo, and (c) administering the cytotoxic T lymphocytes to the subject, wherein the HPV-associated cancer in the subject is inhibited.

23. A method for inhibiting an HPV-associated cancer in a subject comprising:

(a) obtaining dendritic cells from the subject, (b) treating the dendritic cells with the composition of claim 10 ex vivo, and (c) administering the treated dendritic cells to the subject, wherein the HPV-associated cancer in the subject is inhibited.

24. A method for inhibiting an HPV-associated cancer in a subject comprising:

(a) obtaining peripheral blood mononuclear cells (PBMCs) from the subject, (b) isolating dendritic cells from the PBMCs, (c) treating the dendritic cells with the composition of claim 9 ex vivo, (d) activating the PBMCs with the treated dendritic cells ex vivo, and (e) administering the activated PBMCs to the subject, wherein the HPV-associated cancer in the subject is inhibited.

25. A method for inhibiting an HPV-associated cancer in a subject comprising:

(a) obtaining peripheral blood mononuclear cells (PBMCs) from the subject, (b) isolating dendritic cells from the PBMCs, (c) treating the dendritic cells with the composition of claim 10 ex vivo, (d) activating the PBMCs with the treated dendritic cells ex vivo, (e) isolating T lymphocytes from the activated PBMCs ex vivo, and (f) administering the isolated T lymphocytes to the subject, wherein the HPV-associated cancer in the subject is inhibited.

* * * * *